United States Patent
Pereira et al.

(10) Patent No.: US 9,964,528 B2
(45) Date of Patent: May 8, 2018

(54) USE OF TRANSITION-METAL OXIDE NANOPARTICLES AS SENSITIVE MATERIALS IN CHEMICAL SENSORS FOR DETECTING OR ASSAYING VAPORS OF TARGET MOLECULES

(71) Applicant: COMMISSARIAT À L'ÉNERGIE ATOMIQUE ET AUX ÉNERGIES ALTERNATIVES, Paris (FR)

(72) Inventors: Franck Pereira, Monts (FR); Natacha Oudot, Tours (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days. days.

(21) Appl. No.: 14/347,918

(22) PCT Filed: Sep. 28, 2012

(86) PCT No.: PCT/EP2012/069238
§ 371 (c)(1),
(2) Date: Jul. 9, 2014

(87) PCT Pub. No.: WO2013/045646
PCT Pub. Date: Apr. 4, 2013

(65) Prior Publication Data
US 2014/0315323 A1 Oct. 23, 2014

(30) Foreign Application Priority Data

Sep. 29, 2011 (FR) .................................. 11 58755

(51) Int. Cl.
| | | |
|---|---|---|
| *G01N 33/00* | (2006.01) | |
| *G01N 29/02* | (2006.01) | |
| *G01N 29/036* | (2006.01) | |
| *G01N 33/22* | (2006.01) | |
| *G01N 21/64* | (2006.01) | |
| *G01N 21/63* | (2006.01) | |
| *G01N 21/77* | (2006.01) | |

(52) U.S. Cl.
CPC ....... *G01N 33/0004* (2013.01); *G01N 21/643* (2013.01); *G01N 29/022* (2013.01); *G01N 29/036* (2013.01); *G01N 33/22* (2013.01); *G01N 2021/7786* (2013.01); *G01N 2291/0255* (2013.01); *G01N 2291/0256* (2013.01); *Y10T 436/206664* (2015.01)

(58) Field of Classification Search
CPC .. G01N 33/0004; G01N 33/00; G01N 29/022; G01N 29/036; G01N 29/02; G01N 29/00; G01N 21/643; G01N 21/6428; G01N 21/64; G01N 21/63; G01N 21/62; G01N 21/00; Y10T 436/206664; Y10T 436/20; Y10T 436/00

USPC .................................................. 436/135, 127
See application file for complete search history.

(56) References Cited

U.S. PATENT DOCUMENTS

| | | | |
|---|---|---|---|
| 5,698,266 A | 12/1997 | HerveFloch et al. | |
| 2007/0212542 A1 | 9/2007 | Guo et al. | |
| 2009/0011293 A1* | 1/2009 | Wood et al. | ..................... 429/17 |
| 2012/0290051 A1* | 11/2012 | Boyden et al. | ............... 607/113 |
| 2013/0260283 A1 | 10/2013 | Valle et al. | |

FOREIGN PATENT DOCUMENTS

| | | |
|---|---|---|
| FR | 2703791 A1 | 10/1994 |
| WO | 2005040756 A2 | 5/2005 |

OTHER PUBLICATIONS

Reedo, Valter, Elaboration of IVB group metal oxide structures and their possible applications, obtained on Dec. 6, 2016, published on-line Oct. 2, 2008, University of Tartu, pp. 1-36.*
Chaudhury et al, Sol-gel Technology for Sensor Applications, Defence Science Journal, vol. 57, No. 3, May 2007, pp. 241-253.*
Althues, H., et al, "Transparent and luminescent YVO4 : Eu/polymer nanocomposites prepared by in situ polymerization", "J. Mater. Chem.", Nov. 23, 2006, pp. 758-765, vol. 17.
Apblett, A., et al., "Nanotechnology for Neutralization of Terrorist Explosives", "Ceramic Nanomaterials and Nanotechnologies IV" (editors R. M. Laine, M. Hu and S. Lu), 2006, pp. 29-35, vol. 172, Publisher: John Wiley & Sons, Inc., Published in: Hoboken, NJ, USA.
Belleville, P., "Functional coatings: The sol-gel approach", "Comptes Rendus Chimie", Feb. 9, 2010, pp. 97-105, vol. 13.
Bohrer, F., et al., "Selective detection of vapor phase hydrogen peroxide with phthalocyanine chemiresistors", "J. Am. Chem. Soc.", Mar. 6, 2008, pp. 3712-3713, vol. 130, No. 12.
Casanova, D., et al., "Single europium-doped nanoparticles measure temporal pattern of reactive oxygen species production inside cells", "Nature Nanotechnology", Aug. 9, 2009, pp. 581-585, vol. 4.
Dimova-Malinovska, D., et al., "Sensitivity of ZnO films doped with Er, Ta and Co to NH3 at room temperature", "physica status solidi (a)", Jul. 17, 2008, pp. 1993-1997, vol. 205, No. 9.
Feofilov, S., et al., "Gaseous environment-sensitive fluorescence of YAG: Ce3+ nanocrystals ", "J. Appl. Phys.", Mar. 18, 2010, pp. 064308-1-064308-7, vol. 107.

(Continued)

*Primary Examiner* — Christine T Mui
(74) *Attorney, Agent, or Firm* — Pearne & Gordon LLP (57) ABSTRACT

The invention relates to the use of nanoparticles of at least one oxide of at least one transition metal doped with a rare earth element, particularly $Y_xVO_4Eu_{1-x}$ nanoparticles obtained through a sol-gel process, as a sensitive material in a chemical sensor for detecting peroxide-compound vapors. The material is used in a liquid process, in a spray of the initial sol, or in a solid thin film after being deposited on a substrate. The inorganic, fluorescent character of the nanoparticles makes it possible to obtain a sensitive material for an optical sensor that has good performance stability over time. The intended uses are the detection of explosives or explosive precursors, particularly peroxides, the control or monitoring of atmospheric pollution and ambient-air quality, and the monitoring of industrial sites.

48 Claims, 3 Drawing Sheets

(56) References Cited

OTHER PUBLICATIONS

Ge, C., et al., "Preparation and gas-sensing properties of Ce-doped ZnO thin-film sensors by dip-coating", "Materials Science and Engineering: B", Feb. 2007, pp. 53-58, vol. 137.

Ge, C. et al "Structural characteristics and UV-light enhanced gas sensitivity of La-doped ZnO nanoparticles", "Materials Science and Engineering: B", Jun. 25, 2007, pp. 43-48, vol. 141.

Germain, M., et al., "Turn-on fluorescence detection of H2O2 and TATP", "Inorg. Chem.", Oct. 2, 2008, pp. 9748-9750, vol. 47, No. 21.

Guzman, C., et al., "Hydrogen peroxide sensor based on modified vitreous carbon with multiwall carbon nanotubes and composites of Pt nanoparticles-dopamine", "Electrochimica Acta", Oct. 18, 2008, pp. 1728-1732, vol. 54.

Hong, J., et al., "Determination of H2O2 and organic peroxides by high-performance liquid chromatography with post-column UV irradiation, derivatization and fluorescence detection", "Fresenius' Journal of Analytical Chemistry", May 1998, pp. 124-128, vol. 361.

Laine, D., et al., "Electrochemical detection of triacetone triperoxide employing the electrocatalytic reaction of iron(II/III)-ethylenediaminetetraacetate and hydrogen peroxide", "Anal Chim Acta", Dec. 8, 2007, pp. 56-60, vol. 608.

Lu, D., et al., "Highly sensitive electrochemical detection of trace liquid peroxide explosives at a Prussian-blue 'artificial-peroxidase' modified electrode", "Analyst", Oct. 12, 2006, pp. 1279-1281, vol. 131.

Malashikhin, S., et al., "Fluorescent signaling based on sulfoxide profluorophores: application to the visual detection of the explosive TATP", "J. Am. Chem. Soc.", Sep. 6, 2008, pp. 12846-12847, vol. 130, No. 39.

Mills, A., et al., "Hydrogen peroxide vapour indicator", "Sensors and Actuators B: Chemical", Dec. 25, 2008, pp. 458-463, vol. 136.

Munoz, R., et al., "'One-step' simplified electrochemical sensing of TATP based on its acid treatment", "Analyst", Apr. 30, 2007, pp. 560-565, vol. 132.

Rouquerol J., et al. , "Recommendations for the characterization of porous solids (Technical Report)", "Pure and Applied Chemistry", Jan. 1994, pp. 1739-1758, vol. 66, No. 8.

Sanchez, J., et al., "Polymerization of a boronate-functionalized fluorophore by double transesterification: applications to fluorescence detection of hydrogen peroxide vapor", "J. Mater. Chem.", Sep. 29, 2008, pp. 5134-5141, vol. 18.

Sanchez-Pedrono, J., et al., "The investigation of coating materials for the detection of nitrobenzene with coated quartz piezoelectric crystals", "Analytica Chimica Acta", 1986, pp. 285-291, vol. 182.

Schulte-Ladbeck, R., et al., "A field test for the detection of peroxide-based explosives", "Analyst", Aug. 16, 2002, pp. 1152-1154, vol. 127.

Senesac, L., et al., "Nanosensors for trace explosive detection", "materialstoday", Mar. 2003, p. 2836 vol. 11, No. 3.

Shu, X., et al., "H2O2 sensor based on the room-temperature phosphorescence of Nano TiO2/SiO2 composite", "Analytical Chemistry", Apr. 20, 2007, pp. 3695-3702, vol. 79, No. 10.

Valeur, B., "Molecular Fluorescence: Principles and Applications, 1st Edition", Dec. 20, 2001, pp. 1-381, Publisher: Wiley-VCH Verlag GmbH, Published in: Weinheim, Germany.

Yao, S., et al., "A hydrogen peroxide sensor based on colloidal MnO2/Na-montmorillonite", "Applied Clay Science", May 2, 2006, pp. 35-42, vol. 33.

Yu, M., et al., "Silica Spheres Coated with YVO4:Eu3+ Layers via Sol-Gel Process: A Simple Method to Obtain Spherical Core-Shell Phosphors", "Chem. Mater.", Mar. 8, 2005, pp. 1783-1791, vol. 17.

Zhou, Q., et al., "An ethanol gas sensor using energy transfer cataluminescence on nanosized YVO4:Eu3+ surface", "Sensors and Actuators B: Chemical", Oct. 29, 2009, pp. 192-197, vol. 144.

\* cited by examiner

USE OF TRANSITION-METAL OXIDE NANOPARTICLES AS SENSITIVE MATERIALS IN CHEMICAL SENSORS FOR DETECTING OR ASSAYING VAPORS OF TARGET MOLECULES

CROSS-REFERENCE TO RELATED APPLICATIONS

This application is a U.S. national phase under the provisions of 35 U.S.C. § 371 of International Patent Application No. PCT/EP12/69238 filed Sep. 28, 2012, which in turn claims priority of French Patent Application No. 1158755 filed Sep. 29, 2011. The disclosures of such international patent application and French priority patent application are hereby incorporated herein by reference in their respective entireties, for all purposes.

TECHNICAL FIELD

The present invention relates to the use of inorganic nanoparticles of transition metal oxides, more precisely nanoparticles of oxide of at least one transition metal doped with a rare earth element, said nanoparticles being obtained through a sol-gel process, as sensitive materials in chemical sensors intended to detect or assay vapors of target compounds or molecules.

Said target compounds or molecules are particularly atmospheric pollutants, explosives or precursors of explosives.

The invention also relates to chemical sensors comprising said nanoparticles as sensitive materials.

The invention relates more particularly to the detection and the assaying of peroxides and particularly hydrogen peroxide.

Hydrogen peroxide is a compound from which it is possible to prepare, in a "hand-made" manner, explosives such as triacetone triperoxide (TATP) or hexamethylene triperoxide diamine (HMTD), and hydrogen peroxide is also a decomposition product of said explosives, consequently the invention finds particularly its application in fighting terrorism.

Peroxides are, furthermore, very unstable compounds that decompose easily while releasing, for a certain number thereof, flammable vapors, and consequently the invention also finds its application in monitoring, for security purposes, the premises in which are manufactured, stored and/or used peroxides or peroxidizable compounds, in other words compounds that, initially, are not peroxides but which are capable of being transformed at least partially into peroxides following a phenomenon of auto-oxidation, also known as peroxidation, as well as in the monitoring of atmospheric pollution.

STATE OF THE PRIOR ART

Peroxides are chemical compounds that comprise one or more —O—O— groups and which have, as a result, a strong oxidizing power.

They are thus widely used as bleaching agents, particularly in the textile industry, for the bleaching of natural fibers such as cotton fibers, and in the paper industry, for the bleaching of paper pulp. They are also widely used as initiators, promoters or catalysts in radical polymerization processes, and as cross-linking or vulcanization agents in the plastic materials industry.

To this must be added uses specific to each peroxide.

Thus, for example, hydrogen peroxide, of formula $H_2O_2$, also known as oxygenated water, is employed as:
  disinfecting agent;
  sterilization agent, particularly in the food processing industry where, vaporized at high temperature, it serves to sterilize composite packaging just before the incorporation of foodstuffs, and in the medical industry where it serves to sterilize heat sensitive medical devices, which thus cannot be sterilized by heat.
  agent for treating domestic or industrial waste water; and as
  gaseous effluent treatment agent.

It turns out that hydrogen peroxide is also capable of being used to manufacture, in a home-made manner, explosive organic peroxides such as TATP or HMTD and that these explosives give off, when they decompose, hydrogen peroxide.

Organic peroxides such as TATP or HMTD are compounds that may be easily synthesized from easily accessible precursors and which are as powerful as TNT.

The instability of said compounds means they cannot be used for military applications but, conversely, said compounds are regularly involved in terrorist acts due to the fact that they are not detectable by the sensors currently in place which are sensitive to nitrated explosives.

It also turns out that peroxides have the particularity of being very unstable compounds and decompose while releasing, for a certain number of them, flammable vapors.

It is thus highly desirable to be able to have available devices making it possible to detect in a reliable but nevertheless rapid manner the presence of home-made explosives or precursors thereof, and in particular the presence of peroxides, particularly when they are in the vapor state, whether to thwart a terrorist threat or to prevent any risk of accident in premises where peroxides or peroxidizable compounds are manufactured, stored and/or used.

In particular, since hydrogen peroxide is both a precursor of organic peroxides and a degradation product of said compounds, it appears vital to be able to detect it.

These explosive compounds and precursors thereof, including $H_2O_2$, generally have very low vapor pressures, consequently the compounds and precursors have to be able to be detected in trace amounts.

Moreover, the intended application being particularly the control of luggage, the detection techniques implemented must be compatible with mass transport.

The methods currently used to detect vapors of compounds, for example peroxides, entering particularly into the composition of explosives, implement analytical devices such as ion mobility spectrometers, mass spectrometers, infrared analyzers or chromatography techniques coupled with a spectrometer.

Generally speaking, these methods give satisfactory results in terms of sensitivity and reliability, which is primordial with regard to the detection of explosives given the very low concentration in vapors in the atmosphere.

However, said methods also have numerous drawbacks such as their high cost, the considerable size and the high energy consumption of the devices that they use, and their complex implementation, which makes the presence of a specialist to interpret the signals obtained indispensable.

Moreover, these methods cannot be used anywhere, and particularly in places and sites that are difficult to access because the devices that they use cannot be made portable and autonomous.

The analysis may also be carried out in the laboratory by the aforementioned devices after having taken samples on site but this method does not enable a rapid response to be obtained.

Resorting to "sniffer dogs" or other animals taught and trained to detect vapors has the drawback of requiring a long period of training the dogs and their masters and excludes continuous and prolonged interventions due to the limited attention span of these animals. In addition, said method also requires the presence of a specialist such as a dog handler for example.

For a certain number of years, the development of sensors capable of detecting in real time species, compounds, chemical molecules, particularly gaseous species, has been in full development.

The functioning of these sensors is based on the use of a sensitive material, in other words a material at least one physical and/or chemical property of which is modified in contact with the searched for species, compounds, chemical molecules also known as target species, compounds, molecules.

Said sensitive material is connected to a system capable of measuring instantaneously any variation of this physical and/or chemical property to thereby highlight the presence of the searched for species, compounds, chemical molecules.

More precisely, the operating principle of said chemical sensors is based on the heterogeneous interaction of the target molecule, for example in gas form, with a sensitive material, particularly in the form of a solid thin layer or sprayed solution, which brings about the variation of at least one physical-chemical property of said material.

Said variation may be of electrical, optical, mechanical or magnetic nature. It may be an evolution of the weight of the sensitive material, due to the adsorption of molecules, particularly the searched for gaseous molecules, at the surface of the sensitive material.

The variation of the property of the sensitive material is then measured in real time then transformed by a suitable transduction system into an exploitable electrical signal.

Said signal is finally transmitted to the measuring device where it undergoes suitable algorithmic treatment in order to indicate the presence or not of the searched for molecules, for example the presence or not of the gaseous molecules searched for in the atmosphere.

The advantages of chemical sensors, particularly compared to the aforementioned methods, are multiple: instantaneousness of results, detection in real time, possibility of miniaturization and, thus, portability, manageability and considerable autonomy, low manufacturing and operating costs, simplicity of use, etc.

Nevertheless, it is obvious that their performances are extremely variable depending on the nature of the sensitive material used.

Thus, for detecting peroxides and in particular hydrogen peroxide, various sensitive materials have been envisaged.

A normal approach for detecting hydrogen peroxide $H_2O_2$ consists in measuring the current when the peroxide is oxidized at a solid electrode.

In order to improve the response, several studies have consisted in coating the surface of the electrode with substances having a catalytic activity such as transition metal oxides [1], enzymes [2], Prussian blue [3] or metal phthalocyanine [4].

Another approach consists in using conductive materials such as carbon nanotubes doped with different elements such as platinum [5] or an EDTA/iron complex [6] for example to improve the electrocatalytic properties.

These analytical techniques make it possible to measure directly the concentration of $H_2O_2$ present in a solution, or instead the concentration of $H_2O_2$ generated when TATP or HMTD are treated by ultraviolet or by a laser beam. It is thereby possible to carry out an indirect detection of said species.

Organic peroxides may also be decomposed in acid medium [7] to form $H_2O_2$.

Although the techniques described above are useful in liquid medium, they appear for the most part little adapted to the detection of peroxide vapors.

Only phthalocyanines [4], deposited in the form of films of 50 nm thickness, enable the detection of $H_2O_2$ in vapor form in ten or so minutes.

Other compounds, organic molecules, whether they are dyes or luminescent compounds, may be deposited in the form of films on substrates, to thereby form test strips capable of detecting peroxides, the presence of which causes a reduction in the luminous intensity emitted by said molecules.

Examples of such molecules are lissamine green (organic dye) encapsulated in polyvinyl alcohol (PVA) [8], or hydrogen and molybdenum bronze (MoHB; $Mo_2O_5(OH)$) [9].

The bleaching observed in the presence of a strong oxidant such as peroxides is due to a degradation of the organic molecule. Said sensors are thus irreversible and exhibit low selectivity, which is responsible for numerous false positives. In addition, since organic molecules are globally not very stable under illumination, said sensors will offer a short lifetime and will not enable continuous operation.

Another method consists in using organic molecules that produce a fluorescence signal during their degradation by $H_2O_2$. This is the case of poly[3',6'-bis(1,3,2-dioxaborinane) fluoran] (PolyF-1) [10], prochelators [11] or pyrene sulfoxides [12].

The advantage of this method is that an onset of fluorescence is visualized, which is much easier to detect than a reduction in fluorescence.

However, this method conserves all of the drawbacks due to the implementation of organic molecules, namely particularly a low lifetime of the sensors.

Inorganic compounds thus seem to be better adapted to the detection of peroxides and sensitive inorganic materials have already been used to detect $H_2O_2$ in solution.

The document of Shu et al. [13] discloses a $TiO_2/SiO_2$ composite prepared by sol-gel process. Under an excitation wavelength of 403 nm, the phosphorescence of the composite drops during the addition of a solution of hydrogen peroxide.

Similarly, the document of Casanova et al. [14] mentions a luminescent probe to detect hydrogen peroxide in aqueous phase which uses a material of $YVO_4$ type doped with europium.

The oxidation of Eu II into Eu III in the presence of $H_2O_2$ then leads to an increase in fluorescence.

Furthermore, it is widely accepted that, for detecting gaseous compounds, the sensitive material must have a high specific surface area in order to favor heterogeneous interactions.

Thus, the use of mesoporous thin films constituted of nanoparticles of silica incorporating probe molecules enables particularly the detection of gaseous nitro-aromatic compounds with a high sensitivity due to a high specific surface area [15].

It is apparent from the foregoing that the sensitive organic materials proposed for chemical sensors, particularly intended for the detection of peroxides, have the major drawback of a very low robustness because they have a very short lifetime when they are subjected to irradiation, in particular when they are exposed to daylight.

Sensitive inorganic materials enable this drawback to be overcome, but although certain sensitive inorganic materials have been proposed for detecting hydrogen peroxide, said detection only relates to hydrogen peroxide in the liquid state.

There thus exists, with regard to the foregoing, a need for a sensitive inorganic material that makes it possible to detect the vapors of peroxides, in other words which is capable of reacting in the presence of peroxides in the vapor state.

There still exists a need for a sensitive material which, when it is used in a chemical sensor, has all the characteristics required for such a material such as the sensitivity (affinity of the sensitive material for the analyte, in the case in point the vapors of peroxides enabling its detection in the form of traces) associated with a rapidity of response, selectivity (sensitivity of the material only to the targeted analyte), reversibility (ability to return to the initial state after detection) which will enable continuous operation, and stability over time and in the conditions of use.

The aim of the present invention is, among other things, to meet the needs and requirements enumerated above.

DESCRIPTION OF THE INVENTION

The subject matter of the present invention, according to a first embodiment, is the use of nanoparticles of at least one oxide of at least one transition metal doped with a rare earth element, obtained through (by) a sol-gel process, as a sensitive material in a chemical sensor for detecting or assaying vapors of one or more target compound(s) or molecule(s), in which the nanoparticles are present in the sensor in the form of a solid thin film of nanoparticles.

Advantageously, the thin film is prepared directly by a wet process by deposition of a sol, especially an aqueous sol, which is the sol in which the nanoparticles have been synthesized, formed.

One thus does not pass through intermediate steps consisting for example in forming a xerogel then grinding and calcinating it to obtain a powder. A paste is then prepared with said powder, then a thick film is prepared with said paste.

In other words, in this first embodiment of the invention, one prepares, synthesizes, the oxide doped in a solvent such as water. For example, as is detailed below, the oxide doped by aqueous process in the presence of salts, is prepared by basic catalysis.

Nanoparticles of said doped oxide are then formed, and they remain dispersed within the sol.

The preparation of the thin film is carried out directly by a wet process by deposition of the sol of nanoparticles, and not by deposition of a paste. The thin film is prepared without going through all of the intermediate steps mentioned above, particularly of preparation of a powder then of a paste.

By carrying out the deposition directly by wet process, from the sol, it is possible to obtain the thin film characteristic of this first embodiment.

The film formed thus has a low thickness, for example 200 nm, and generally a high specific surface area, for example 100 m$^2$/g to 200 m$^2$/g, on account of the assembly of nanoparticles that have a very low size, such as defined hereafter, for example a size of 10 to 20 nm, and which each comprises crystallites of several nanometers, for example 1 to 5 nm.

The low thickness of the film, and optionally its high specific surface area, are characteristics which contribute in an important or even decisive manner to obtaining a sensor having the advantageous properties enumerated hereafter particularly in terms of sensitivity and selectivity.

It is precisely because the film is prepared directly by wet process by deposition of a sol, particularly aqueous, which is the sol in which the nanoparticles have been synthesized, formed, that it has these advantageous characteristics and properties.

The deposition of a paste prepared from a powder does not make it possible to obtain a film according to the invention, thin and generally of high specific surface area.

It has been noted that the preparation of the oxide doped by aqueous process in the presence of salts by basic catalysis was a process which was particularly advantageous for obtaining a film according to the invention, thin and of high specific surface area.

Transition metal is taken to mean all elements having an atomic number of 21 to 30; 39 to 48; and 72 to 80.

Preferred transition metals are vanadium and yttrium.

The oxide may be a simple oxide, of a single transition metal, such as vanadium, or instead a mixed oxide of two transition metals such as vanadium and yttrium, or instead an oxide of more than two transition metals.

Rare earth is taken to mean all elements having an atomic number of 57 to 71 or lanthanides.

Preferred rare earths are europium, erbium or ytterbium.

"Doped with a rare earth element" is generally taken to mean that said rare earth represents 1% to 30% by weight of the total weight of the oxide.

Herein, the notation $VO_4$:Eu, for example, means that $VO_4$ is doped with europium in all proportions.

In the same way, the notation $YVO_4$:Eu means that $YVO_4$ is doped with europium in all proportions.

The use of inorganic, mineral nanoparticles, of an oxide of at least one transition metal doped with a rare earth element, obtained through a sol-gel process, as a sensitive material in a chemical sensor for detecting or assaying vapors of one or more target compound(s) or molecule(s) and more particularly vapors of peroxide, particularly of hydrogen peroxide, said nanoparticles being in the sensor in the form of a solid thin film of nanoparticles, has never been either mentioned or suggested in the prior art.

The use of nanoparticles of vanadium oxide doped with europium as solid material for the optical storage of data, in nano-emitters of red light for lamps, or as material for solar concentrators, is certainly mentioned respectively in the documents [16], [17], and [18]. In these documents, the nanoparticles are never associated with a transduction device in order to constitute a chemical sensor of gas capable particularly of detecting vapors of peroxides.

The use that is the subject matter of the invention, in this first embodiment, makes it possible to meet the needs and requirements enumerated above. The same is true for the second embodiment described hereafter.

Advantageously, the nanoparticles are nanoparticles of $Y_xVO_4Eu_{1-x}$, where x has a value of 0 to 0.995.

Preferably, the nanoparticles are selected from the nanoparticles of $VO_4Eu$, in other words x=0 in the formula $Y_xVO_4Eu_{1-x}$, and the nanoparticles of $Y_{0.5}VO_4Eu_{0.5}$, in other words x=0.5 in the formula $Y_xVO_4Eu_{1-x}$.

The sol-gel technique is a well-known technique to the man skilled in the art and will not be described in a detailed manner herein.

It may simply be recalled that this technique consists in a mineral polymerization in solution generally carried out in mild temperature and pressure conditions.

It comprises a reaction of hydrolysis of one or more precursor(s) of oxide in a solvent phase to form reactive hydroxyl functions, groups.

These hydroxyl functions, groups then react by condensation reactions to form "oxo" bridges in other words "metal-oxygen-metal" bridges by elimination of molecules of water or alcohol.

Thus, for example, in the case of organic precursors of oxide of a metal or metalloid M, said reactions may be written schematically:

Hydrolysis: M-OR+H$_2$O→M-OH+R—OH

Condensation: M-OH+RO-M→M-O-M+R—OH

M-OH+HO-M→M-O-M+H$_2$O.

These hydrolysis-condensation reactions lead firstly to the formation of a solution which is called "sol" but which may be, according to the conditions in which is carried out the hydrolysis of the precursors of oxide, either a sol in the strict sense of the term (in other words a solution containing chemical species in the form of colloids), or a solution containing chemical species in the form of oligomers or polymers, then to the formation of a "gel" (in other words a viscous mass, elastic and having a frozen liquid structure) which is constituted of a mineral polymeric network and the viscosity of which increases with time.

After elimination of the solvent phase entrapped in the gel, the latter may be subjected to complementary treatments such as, for example, a heat treatment making it possible to densify it.

Advantageously, the nanoparticles particularly of Y$_x$O$_4$:Eu$_{1-x}$ may have a size, defined by their largest dimension, for example by their diameter, of 2 to 100 nm, preferably 10 nm to 20 nm.

In fact, the nanoparticles implemented according to the invention generally have a spherical or quasi-spherical, spheroidal shape.

According to the first embodiment, the nanoparticles are in the sensor in the form of a solid thin film of nanoparticles.

Advantageously, said solid thin film of nanoparticles covers at least in part one or both faces of a flat (planar) substrate.

Advantageously, the solid thin film of nanoparticles has a thickness of 2 nanometers to 10 micrometers, preferably 2 nanometers to one micrometer, even more preferably 100 nm to 300 nm, for example 200 nm.

Advantageously, said solid thin film of nanoparticles is a mesoporous film.

In the present, "mesoporous film" is generally taken to mean a film, the size of the pores of which is comprised between 2 and 50 nanometers, according to the recommendations for the characterization of porous solids of the International Union of Pure and Applied Chemistry (IUPAC) [20].

Such a mesoporosity also contributes in an important or even decisive manner to obtaining a sensor having the advantageous properties mentioned, particularly in terms of sensitivity and selectivity.

Advantageously, the solid thin film of nanoparticles may have a specific surface area of 100 m$^2$/g to 200 m$^2$/g, measured by BET.

Said solid thin film may preferably be obtained through deposition of one or more layer(s) of a sol of nanoparticles, preferably an aqueous sol, on at least one of the faces of a flat substrate and elimination of the solvent phase present in said layer or said layers. Said film generally has a thickness in the aforementioned range after elimination of the solvent.

Said film is qualified as solid film, precisely because the solvent has been totally or substantially eliminated therefrom. The solvent content of said solid thin film is generally below 1% by weight, preferably it is 0% by weight.

Said sol, typically contains colloids, nanoparticles, of oxide of at least one transition metal doped with a rare earth element, for example of oxide of vanadium and yttrium doped with europium having a size, defined by their largest dimension, for example by their diameter, of the order of 2 nanometers to 100 nanometers, preferably 10 nm to 20 nm.

Said sol, named colloidal sol, is preferably prepared by basic hydrolysis of the precursors of oxides in aqueous phase.

Advantageously, the precursors are selected from metal salts such as nitrates.

Examples of precursors are europium nitrate, sodium orthovanadate and yttrium nitrate.

In order to limit the growth of particles and to assure their dispersion, a solution of a dispersant such as sodium citrate may be added to the reaction mixture.

The elimination of ions in excess from the sol may be carried out by dialysis using for example a semi-permeable membrane.

During this step of elimination of ions in excess, for example by dialysis, it is also possible to replace all or part of the water by an organic solvent.

Said organic solvent may be selected for example from aliphatic alcohols with 1 to 6C such as methanol, ethanol, and isopropanol; acetonitrile; tetrahydrofuran (THF); toluene; and mixtures thereof.

Whatever the chosen synthesis process, namely basic hydrolysis of a precursor of oxides in aqueous phase, or other, a stable, transparent and colorless sol is obtained. The concentration of the final sol is finally adjusted by addition or evaporation of solvent.

The colloidal sol of oxides obtained thus comprises a solvent generally selected from water; 1 to 6C aliphatic alcohols such as methanol, ethanol, and isopropanol; acetonitrile; tetrahydrofuran (THF); toluene; and mixtures thereof.

A final sol that comprises other than water an organic solvent, for example a final sol containing a mixture of water and acetonitrile, preferably in equal proportions, conserves the stability and all the properties of the aqueous sol such as fluorescence properties, but has the advantage of enabling the solubilization of organic peroxides such as TATP.

The colloidal sol has advantageously a concentration of nanoparticles of 0.1% to 10% by weight, preferably 0.1% to 4% by weight, even more preferably 2% to 4% by weight.

The deposition of the layer or layers of the sol of colloidal oxides on the substrate may advantageously be carried out by a technique of deposition by a wet process.

This technique of deposition by a wet process may be selected from one of the following techniques of deposition by a wet process:
spray coating;
spin coating;
drop coating;
dip coating;
meniscus coating;
soak coating;

inkjet printing;
roll to roll process; or else
paint coating.

Among these techniques, which are well known to those skilled in the art, spray coating, spin coating, dip coating and drop coating are preferred because it is these that are best suited to the formation of a thin film by deposition of a sol of colloidal oxides on a substrate.

Dip coating and spin coating are further preferred because these techniques make it possible to obtain homogeneous thin films.

Whatever the deposition technique used, the solvent phase, comprising one or more solvent(s) present in the layer or the layers deposited on the substrate is, preferably, eliminated by evaporation, this being able to take place naturally in the open air or being able to be facilitated, for example, by the application of a gaseous flow, by thermal or radiative heating (UV, IR or micro-waves) provided that said heating does not alter the underlying substrate, or instead by mechanical means such as during a deposition of the sol of colloidal oxides on the substrate by spin coating.

The thin film of nanoparticles of oxide of at least one transition metal doped with a rare earth element, such as $Y_xVO_4Eu_{1-x}$, where x is as defined above, may moreover be subjected to one or more treatment(s) selected from:
 a densification by thermal or radiative process (UV, IR or micro-waves); or
 a hardening by chemical process.

Densification by thermal process, which consists in heating the thin film of nanoparticles of oxide to a high temperature, in other words up to 900° C., but nevertheless below the temperature of damaging the substrate, enables said thin film to be consolidated.

Hardening by chemical process, which is disclosed in FR-A-2 703 791 [19], consists in making the thin film of nanoparticles of oxide undergo an alkaline treatment in liquid or gaseous medium, typically in the presence of molecules of ammonia, or an acid treatment.

Advantageously, the nanoparticles of oxide of at least one transition metal doped with a rare earth element, such as $Y_xO_4:Eu_{1-x}$, may each be covered, coated, with a thin layer of silica obtained through sol-gel process.

Said nanoparticles are nanoparticles with core-shell structure in which the core is constituted of a nanoparticle of oxide of at least one transition metal doped with a rare earth element, such as $Y_xVO_4:Eu_{1-x}$, and the shell is constituted of a thin layer of silica.

Said thin layer of silica generally has a thickness of 1 to 10 nanometers.

Such a thickness is generally sufficient and will make it possible on the one hand to increase the stability of the particles in acid medium and on the other hand to graft organic groups capable of improving the performances of the chemical gas sensor, for example its sensitivity, its selectivity and its resistance to ambient humidity.

Said thin layer of silica is preferably obtained through growth in solution of silica on the surface of the nanoparticles of oxide of at least one transition metal doped with a rare earth element such as europium, for example on the surface of the nanoparticles of $Y_xVO_4Eu_{1-x}$.

To do so, it is possible for example to add a precursor of silica such as TEOS to a sol, for example a hydro-alcoholic sol containing nanoparticles of oxide of at least one transition metal doped with a rare earth element such as europium, for example a sol containing nanoparticles of $Y_xVO_4Eu_{1-x}$.

In the presence of a catalyst which may be an acid or a base, a thin layer of silica coats the nanoparticles of oxide of at least one transition metal doped with a rare earth element such as europium, for example nanoparticles of $Y_xVO_4Eu_{1-x}$.

A sol of core-shell nanoparticles is thereby obtained.

This sol, which contains typically colloids or nanoparticles of oxide of at least one transition metal doped with a rare earth element such as europium, for example colloids of $Y_xVO_4Eu_{1-x}$ covered with silica having a diameter of the order of 2 nanometers to 100 nanometers, preferably 10 to 20 nm, may thus, preferably, be prepared by basic hydrolysis of at least one precursor of silicon oxide in a solvent phase containing an organic solvent, alone or mixed with water, and the nanoparticles of oxide of at least one transition metal doped with a rare earth element such as europium, for example nanoparticles of $Y_xVO_4Eu_{1-x}$, then ageing the solution thus obtained.

In this case, the thin layer of silica is most preferably prepared by a process of growth in solution of the silica that comprises the following steps:
 a) a sol of nanoparticles of oxide of at least one transition metal doped with a rare earth element such as europium, for example nanoparticles of $Y_xVO_4Eu_{1-x}$, is prepared in a solvent constituted of an alcohol or a mixture of alcohols;
 b) to the sol prepared in step a) is added at least one precursor of silica, and at least one strong base playing the role of catalyst, such as ammonia, such that the sol has a pH at least equal to 8;
 c) the hydrolysis of said at least one precursor of silica in the alcohol or the mixture of alcohols to which has been added at least one strong base, such as ammonia, and having a pH at least equal to 8, is carried out, whereby a thin layer of silica forms on the particles of oxide of at least one transition metal doped with a rare earth element;
 d) the ageing of the solution thus obtained is carried out to form an alcoholic sol of nanoparticles of oxide coated with a thin layer of silica, and optionally
 e) the strong base is eliminated from the alcoholic sol thus formed or all or part of the alcohol or the alcohols present in said sol is replaced by water.

Thus, the sol of nanoparticles of oxide of at least one transition metal doped with a rare earth element such as europium, for example the sol of nanoparticles of $Y_xVO_4:Eu_{1-x}$ covered with silica, may also be an alcoholic sol, a hydro-alcoholic sol or an aqueous sol.

The elimination of the strong base of the sol obtained at step d) above may be carried out by treating the latter under reflux by an organic solvent, for example an alcohol or a mixture of alcohols.

As for the replacement by water of all or part of the alcohol or alcohols present in the sol obtained at step d) above, this may be carried out by dilution of said sol by a mixture of water and one or more alcohol(s) to obtain a hydro-alcoholic sol, then by concentration of the hydro-alcoholic sol thereby obtained in conditions which make it possible to eliminate all or part of the alcohol or alcohols that it contains.

Advantageously, the thin layer of silica is prepared in alcoholic medium with a controlled water and ammonia content.

In a variant, the sol of particles of oxide of at least one transition metal doped with a rare earth element such as europium, for example the sol of nanoparticles of $Y_xVO_4Eu_{1-x}$, may be coated with a thin layer of silica prepared by acid hydrolysis (in other words that an acid is used instead of a strong base such as ammonia) of at least one precursor of oxide of silicon in solution in a solvent phase containing an organic solvent, alone or mixed with water, and the pH of which is, preferably, comprised between 0 and 1, then mixing the solution thereby obtained with a solution containing water, an organic solvent, and maturing the resulting mixture.

Whatever the hydrolysis process chosen, the precursor of oxide of silicon is, preferably, selected from tetra-functional alkoxides of silicon of formula $Si(OR)_4$ (tetraalkoxysilanes) in which R represents an alkyl group comprising 1 to 6 carbon atoms and, particularly, from tetramethylortho-silicate (TMOS) and tetraethylorthosilicate (TEOS).

Nevertheless, other types of precursor of oxide are also capable of being used such as, for example:

tetra-functional alkoxides of formula $Si(OR)_4$ in which R is a group other than an alkyl group, such as an acetyl group;

mono-, di- or tri-functional silicon alkoxides of formula $Si(OR)_{4-x}R'_x$ in which R is a $C_1$-$C_6$ alkyl group, whereas R' is an organic or inorganic group, for example a chlorine atom, and x is equal to 1, 2 or 3; or else inorganic silicates such as $SiCl_4$, $SiBr_4$ or $Si_3O_7Na_2$.

The organic solvent is, for its part, preferably, an alcohol or a mixture of alcohols, in particular an aliphatic alcohol or a mixture of aliphatic alcohols comprising from 1 to 6 carbon atoms such as methanol, ethanol or isopropanol.

Nevertheless, other types of organic solvents may also be used such as, for example, phenols or diols of formula OH—R"—OH in which R" is a $C_2$-$C_{30}$ alkylene group or a phenyl group.

Furthermore, the sol of nanoparticles of oxide of at least one transition metal doped with a rare earth element, such as $Y_xO_4$:$Eu_{1-x}$, covered with silica has advantageously a content, concentration by weight of nanoparticles of 0.1% to 10%, preferably 0.1% to 4%, and even more preferably 2% to 4% (the content is the same as for the sol, the nanoparticles of which are not covered with silica).

The deposition of the layer or layers of the sol on nanoparticles of oxide of at least one transition metal doped with a rare earth element, but this time coated with silica, on the substrate, may be carried out by a wet process deposition technique and particularly by one of the wet process deposition techniques already cited above.

Whatever the deposition technique used, the solvent phase present in the layer or layers deposited on the substrate is, preferably, removed by evaporation, said evaporation being able to take place naturally in the open air or being able to be facilitated, for example by the application of a gaseous flow, by thermal or radiative heating (UV, IR or micro-waves) provided that said heating does not alter the underlying substrate, or instead by mechanical means such as during a deposition of the sol of nanoparticles of oxide of at least one transition metal doped with a rare earth element such as europium, for example of the sol of nanoparticles of $Y_xVO_4Eu_{1-x}$ covered with silica on the substrate by spin coating.

According to the invention, and as has already been indicated above, the silica may be functionalized by chemical groups for example chemical groups capable of improving the performances of the chemical sensor, for example by reinforcing its sensitivity and/or its selectivity vis-à-vis certain compounds such as peroxides, by increasing its reversibility and/or its durability, or by reducing its sensitivity to environmental hygrometric variations, or instead by improving the robustness thereof, its resistance to ambient humidity.

Thus, the sensitivity and the selectivity of the chemical sensor vis-à-vis peroxide compounds may be reinforced by grafting of chemical groups having a strong affinity for this type of compound, in which case said grafting is, for example, carried out by making the free hydroxyl groups of the silica react with a compound of formula $X_{(4-x-y-z)}$—$SiR^1_xR^2_yR^3_z$ in which X is a hydrolysable group such as a halide, an acetonate, an acrylate or an alcoholate of formula $OR^4$ where $R^4$ is an alkyl group comprising 1 to 10 carbon atoms, $R^1$, $R^2$ and $R^3$, which may be identical or different, are groups sensitive to peroxide compounds, for example of the metal phthalocyanine type, x, y and z are whole numbers ranging from 0 to 3, providing nevertheless that one at least of x, y and z is different to 0 and that x+y+z≤3.

The sensitivity of the chemical sensor to environmental hygrometric variations may, for its part, be reduced by grafting of hydrophobic groups and, particularly, of alkyl groups, of aromatic groups (phenyls for example) or fluorinated groups such as, for example, alkyls chains comprising several atoms of fluorine of —$CH_2$—$CH_2$—$(CF_2)_7$—$CF_3$ type, in which case said grafting is, for example, carried out by making the free hydroxyl groups of the silica react with a compound of formula $X_{(4-x-y-z)}$—$SiR^1_xR^2_yR^3_z$ in which X, x, y and z have the same signification as previously, but in which $R^1$, $R^2$ and $R^3$ are hydrophobic groups.

Advantageously, the functionalization, the grafting, of the silica may take place by reacting the free hydroxyl groups of the silica with a compound of alkoxy silane type (1 to 10C) having at least one non-hydrolysable group bonded to the silicon.

Whatever the chemical groups that it is intended to graft on the silica, the grafting of these groups may be carried out on the nanoparticles of at least one oxide of at least one transition metal, such as $Y_xVO_4$:$Eu_{1-x}$, covered with silica whether they are in the colloidal sol state, before it is deposited on the substrate, or in the form of a solid thin film (solvent eliminated), once said film has been constituted on the substrate.

In the latter case, the grafting is carried out by placing said thin film in contact with a compound comprising at least one group corresponding to those that it is wished to graft, either in vapor form if the compounds that it is wished to graft are volatile, or in liquid form if they are not.

For example, the thin layer of silica, constituted on the nanoparticles, could be soaked in an alcoholic solution containing the species to be grafted and a strong base such as ammonia.

Furthermore, independently of any functionalization of the silica, the thin layer of silica on the nanoparticles may be subjected to one or more treatment(s) selected from:

washing by an organic solvent;

densification by a thermal or radiative (UV, IR or micro-waves) process; or else hardening by chemical process.

Densification by a thermal process, which consists in heating the thin layer of silica, at a high temperature, in other words able to go up to 900° C., but nevertheless below the temperature of damaging the substrate, makes it possible to consolidate said thin layer.

Hardening by chemical process, which is disclosed in FR-A-2 703 791 [19], consists in making the thin layer of silica undergo an alkaline treatment in liquid or gaseous medium, typically in the presence of molecules of ammonia, or an acid treatment. This makes it possible to improve not only the mechanical strength of said thin layer and, in particular, its abrasion resistance and its adhesion on the substrate, but also the detection performances of the chemical sensor.

According to a second embodiment, the nanoparticles are present in the sensor in the form of a sol of nanoparticles of at least one oxide of at least one transition metal doped with a rare earth element, such as $Y_xVO_4$:$Eu_{1-x}$, obtained through (by) a sol-gel process, in a solvent.

The subject matter of the present invention, according to this second embodiment, is the use of nanoparticles of at least one oxide of at least one transition metal doped with a rare earth element, obtained through a sol-gel process, as a sensitive material in a chemical sensor for detecting or assaying vapors of one or more target compound(s) or molecule(s); in which the nanoparticles are present in the sensor in the form of a sol of nanoparticles in a solvent.

This second embodiment of the invention, where the nanoparticles are present in the sensor in the form of a sol of nanoparticles, involves a liquid-gas interaction whereas the first embodiment of the invention, in which the nanoparticles are present in the sensor in the form of a solid film of nanoparticles, involves a solid-gas interaction.

In other words, the invention also relates to the direct use of generally colloidal sols containing inorganic nanoparticles of at least one oxide of at least one transition metal doped with a rare earth element, for example nanoparticles of $Y_xVO_4$:$Eu_{1-x}$, obtained through a sol-gel process as a sensitive material in a chemical sensor for detecting or assaying vapors of one or more target compound(s) or molecule(s) such as peroxides.

Such a sol containing nanoparticles of at least one oxide of at least one transition metal doped with a rare earth element, for example nanoparticles of $Y_xO_4$:$Eu_{1-x}$, obtained through a sol-gel process, as well as its preparation, have already been described above.

Said sol typically contains colloids of at least one oxide of at least one transition metal doped with a rare earth element such as europium having a size, defined by their largest dimension such as their diameter, of the order of 2 nanometers to 100 nanometers.

The nanoparticles of oxides of this sol have also already been described above. Said nanoparticles may, as has already been mentioned above, optionally be provided with a thin layer of silica and said thin layer may optionally be functionalized as has already been described.

Said colloidal sol of oxides comprises a solvent selected generally from water; organic solvents such as 1 to 6C aliphatic alcohols such as methanol, ethanol, and isopropanol, acetonitrile, tetrahydrofuran (THF), toluene; and mixtures thereof.

The sol used in this second embodiment has advantageously a concentration of nanoparticles of 0.01% to 4% by weight.

The concentration of this sol, used in this second embodiment, is much lower than the concentration of the sol used to prepare the solid thin film in the first embodiment.

Said sol may be used directly. It is then placed in contact with a gaseous atmosphere, for example an atmosphere or a volume of air to be analyzed with a view to detecting or assaying vapors of target compounds or molecules, in particular vapors of atmospheric pollutants, such as vapors of peroxides, likely to be found in said gaseous atmosphere.

This bringing into contact of sol-gases may take place for example by spraying, nebulizing the sol, in the form of a jet, nebulisate or spray in the gaseous atmosphere to be analyzed, or by placing the sol in a vessel and by bringing into contact, for example by bubbling the gaseous atmosphere, the gas with the liquid sol.

This placing in contact is generally coupled with an optical detection using the variation of the fluorescence intensity of the material.

Or instead, the sol of nanoparticles is in the form of a thin film, for example a thin film covering at least in part one or both faces of a flat substrate.

It is then generally necessary to take care that the solvent does not evaporate.

Said substrate may be for example a substrate of quartz microbalance type for a gravimetric sensor or instead a quartz or glass slide for an optical sensor.

Advantageously, the thin film of the sol of nanoparticles has a thickness of 2 nanometers to 10 micrometers, preferably 2 nanometers to one micrometer.

The deposition of the film of sol may be carried out by one of the techniques already mentioned above within the scope of the description of the preparation of a solid thin film of nanoparticles. It is nevertheless important to note that, in this embodiment, the solvent phase present in the film is not eliminated because this is a film of the sol and not a solid film.

Or instead, the sol may be placed in a vessel or recipient advantageously provided with a removable cover which limits the evaporation of the solvent.

According to the invention, generally speaking, not just in the first embodiment but also in the second embodiment, the substrate, as well as the measurement system that is associated with it, are selected as a function of the physical property of the solid thin film of nanoparticles of metal oxides or the thin film of sol, the variations of which induced by the presence of one or more target compound(s), particularly one or more compound(s) of peroxide type, are intended to be measured by the chemical sensor.

Preferably, the variations in weight and the variations in fluorescence of this thin film are measured.

Also, the chemical sensor is, preferably, a gravimetric sensor or a fluorescence optical sensor.

As examples of gravimetric sensors, may be cited microbalance sensors, SAW (surface acoustic wave) sensors such as Love wave sensors and Lamb wave sensors, and microlevers.

Among gravimetric sensors, more particularly sensors of the quartz microbalance type are preferred.

This type of sensor, the operating principle of which has been described by Sanchez-Pedrono et al. (*Anal. Chem. Acta*, 182, 1986, page 285, [21]), comprises, schematically, a piezo-electric substrate (or resonator), generally a crystal of quartz covered on both of its faces with a metal layer, for example gold or platinum, and which is connected to two electrodes. Since the sensitive material covers one or both faces of the substrate, any variation in weight of said material results in a variation in the vibration frequency of the substrate.

The operating principle of fluorescence optical sensors has, for its part, been described by Valeur in *Molecular Fluorescence: Principles and Applications*, 2002, Ed. WILEY VCH, New York [22]. This type of sensor generally comprises a glass substrate of optical quality, one of the faces of which is covered with a thin film of the sensitive material. The intensity of the fluorescence emitted by the sensitive material may be measured over the whole of the emission spectrum of said material. Nevertheless, it is preferable to carry out the fluorescence intensity measurements at the emission wavelength giving the maximum intensity values for the excitation wavelength leading, for its part, to the best signal/noise ratio for the acquisition of fluorescence intensities.

The chemical sensor may also be a multisensor, in other words it may comprise several elementary sensors that are provided with sensitive materials, with substrates and/or with measuring systems different to each other.

The multisensor may comprise for example several elementary sensors selected from gravimetric sensors and fluorescence optical sensors, the essential point being that one at least of these elementary sensors is a sensor that comprises nanoparticles of at least one oxide of at least one transition metal doped with a rare earth element obtained through a sol-gel process as a sensitive material; said nanoparticles being able to be in the form of a thin film of nanoparticles, for example $Y_xO_4:Eu_{1-x}$ such as described previously, or a sol of nanoparticles, for example of $Y_xO_4:Eu_{1-x}$.

According to the invention, the target compound(s) or molecule(s) intended to be detected by the chemical sensor is (are) preferably selected from atmospheric pollutants such as $H_2O_2$, explosives and precursors of explosives.

Even more preferably, the target compound(s) or molecule(s) intended to be detected by the chemical sensor is (are) selected from peroxides.

Advantageously, according to the invention, the selective detection or assaying of peroxides vis-à-vis volatile organic compounds is carried out.

According to the invention, the peroxides intended to be detected by the sensor are, preferably, peroxides of which at least one of the two oxygen atoms of the group or of one of the —O—O— groups that they comprise is bonded to a hydrogen atom, whereby said oxygen atom forms a hydroxyl group with said hydrogen atom.

Peroxides that meet this criterion are particularly hydrogen peroxide, hydro-peroxides such as, for example, t-butyl hydroperoxide, α-cumyl hydroperoxide or/and 1-phenethyl hydroperoxide, peroxides of ketones such as, for example, methylethylketone peroxide, acetylacetone peroxide, cyclohexanone peroxide, acetone peroxide (acetone diperoxide $C_6H_{12}O_4$, acetone triperoxide—or triacetone triperoxide—$C_9H_{18}O_6$ and acetone tetraperoxide $C_{12}H_{24}O_8$), and hexamethylene diamine triperoxide, hydrogen peroxide being particularly preferred.

The use of nanoparticles of $Y_xO_4:Eu_{1-x}$, obtained through a sol-gel process as a sensitive material in a chemical sensor for detecting or assaying vapors of one or more target compound(s) or molecule(s) such as peroxides has proved to have numerous advantages that have been highlighted during tests carried out with this material which are particularly described in the examples that follow.

These advantages are particularly the following:
the sensors provided with such a sensitive material are capable of detecting specifically vapors of peroxides, and in particular vapors of hydrogen peroxides, with a very great sensitivity since they can detect their presence at concentrations in air of the order of one ppm (parts per million) and even lower;
the sensors provided with said sensitive material are characterized in particular by:
rapidity of response and reproducibility of said response;
selectivity vis-à-vis peroxidized compounds;
stability of their performances over time and a very satisfactory lifetime;
stability of their performances over a wide range of ambient hygrometry;
an ability to function continuously;
simplicity of manufacture linked to the fact that the sol-gel process is a process that is simple to implement;
a cost compatible with mass production of sensors; and
the possibility of being miniaturized and, thus, to be easily transportable and which can be handled on any type of site.
the material is constituted of particles of nanometric size, which confers to the thin film, generally mesoporous, obtained, or to a sol containing said nanoparticles sprayed in droplets, a large exchange surface area with the gaseous atmosphere;
the interaction takes place directly between the target compound and the sensitive material as of ambient temperature.

The detection may particularly be characterized by a variation in the fluorescence intensity of the material.
the inorganic nature of the sensitive material, constituted of metal oxides, confers to it a robustness much greater than that of organic materials, in particular great performance stability over time and under irradiation, particularly to daylight, with for example, fluorescence intensity conserved for lifetimes longer than three months, whether the material is in the form of a sol or a solid thin film;
the sensitive material, in particular when it involves compounds of the type $Y_xVO_4:Eu_{1-x}$, has advantageously fluorescence properties when it is subjected to ultraviolet radiation. This characteristic enables the use of said material in an optical sensor for detecting peroxides, and in particular vapors of hydrogen peroxide, by extinction of the fluorescence.

In fact, these compounds are characterized by an extremely rapid reduction of their fluorescence intensity in the presence of peroxides in the form of vapors.

The reduction in the fluorescence intensity in the presence of peroxide is due to the heterogeneous interaction between the vapors of the analyte such as the peroxide and the sensitive material inhibiting the transfer of energy from the oxide of transition metal such as a vanadate to the rare earth such as europium responsible for the fluorescence.

Such a sensor is then very sensitive, selective vis-à-vis particularly volatile organic compounds (such as alcohols, ketones, cyclic aromatic compounds or hydrocarbons), and provides a rapid, reliable, and reproducible response.

It should be pointed out that "selective vis-à-vis volatile organic compounds" is generally taken to mean that the sensor makes it possible to detect selectively peroxides in a gas also comprising volatile organic compounds. This selectivity is shown in example 7, below.

Finally, the fluorescence emission of europium around 617 nm provides a visual response which favors the interpretation of the detection.

The invention further relates to a chemical sensor that comprises nanoparticles of at least one oxide of at least one transition metal doped with a rare earth element, obtained through a sol-gel process, as a sensitive material.

In a first embodiment of this chemical sensor, which comprises nanoparticles of at least one oxide of at least one transition metal doped with a rare earth element, obtained through a sol-gel process, as a sensitive material; the nanoparticles are present in the sensor in the form of a solid thin film of nanoparticles.

In a second embodiment of this chemical sensor, which comprises nanoparticles of at least one oxide of at least one transition metal doped with a rare earth element, obtained through a sol-gel process, as a sensitive material; the nanoparticles are present in the sensor in the form of a sol of nanoparticles in a solvent.

Said sensor, both in the first embodiment and in the second embodiment, may be a gravimetric sensor, preferably a quartz microbalance sensor or a fluorescence sensor.

The sensor is preferably intended to detect hydrogen peroxide.

The sensors according to the invention find their application for detecting primary or homemade explosives or precursors of explosives, whether with a view to assuring the safety of public places (airports, underground stations, train stations), controlling the lawfulness of goods circulating in a territory, combating terrorism or instead cleaning up industrial sites. They are also useful for the protection of the environment, in particular for the control and the monitoring of atmospheric pollution and the quality of more or less confined ambiances, as well as for monitoring for security purposes industrial sites that manufacture, store or handle peroxide compounds.

Other characteristics and advantages of the invention will become clearer on reading the complement of description that follows, which relates to examples illustrating the preparation of sols of nanoparticles of $EuVO_4$ and $Y_{0.5}VO_4$:$Eu_{0.5}$, the preparation of a thin film of nanoparticles of $EuVO_4$, the use for detecting vapors of hydrogen peroxide of fluorescence sensors comprising said solid thin film, and the demonstration of the selectivity, the sensitivity and the stability over time of said sensors.

Obviously, the examples that follow are only given by way of illustration of the subject matter of the invention and do not constitute in any way a limitation of said subject matter.

BRIEF DESCRIPTION OF THE DRAWINGS

On the abscissa is plotted the emission wavelength of the solutions (in nm), and on the ordinate is plotted the fluorescence intensity (in arbitrary units).

FIG. 2 represents the absorption (FIG. 2A) and emission (FIG. 2B) spectra of a solid thin film constituted of nanoparticles of $EuVO_4$.

On the abscissa is plotted the absorption (FIG. 2A) or emission (FIG. 2B) wavelength of the thin film (in nm), and on the ordinate is plotted the transmission (in %) or the fluorescence intensity (in arbitrary units) (Example 6).

On the abscissa is plotted the time (in seconds), and on the ordinate is plotted the fluorescence intensity at 617 nm (in arbitrary units).

On the abscissa is plotted the time (in seconds), and on the ordinate is plotted the fluorescence intensity at 617 nm (in arbitrary units).

DETAILED DESCRIPTION OF PARTICULAR EMBODIMENTS

Examples

Example 1

In this example, an aqueous sol of nanoparticles of $EuVO_4$ (x=0 in the formula indicated above) is prepared.

Firstly aqueous solutions containing the precursors of oxides are prepared, namely on the one hand a solution of europium nitrate and on the other hand a solution of sodium orthovanadate, then these solutions are mixed at 60° C.

The solution of europium nitrate, the concentration of which is 0.1 M, is prepared by dissolution of 1.71 g of $Eu(NO_3)_3$, 5 $H_2O$ in 40 mL of water.

The solution of sodium orthovanadate, the concentration of which is 0.1 M, is prepared from 0.55 g of $Na_3VO_4$ which are poured into 30 mL of water. The pH of the solution of $Na_3VO_4$ is controlled and adjusted if necessary to a value comprised between 12.3 and 12.8 by addition of sodium hydroxide.

The solution of europium nitrate is introduced into a round-bottomed two-necked flask surmounted by a condenser and a dropping funnel.

The solution of sodium orthovanadate is placed in said a dropping funnel and added drop by drop to the contents of the round-bottomed two-necked flask, under magnetic stirring. After addition of all the solution of orthovanadate, the sol obtained is left to stir for 30 minutes at 60° C., during which time the reaction between europium nitrate and sodium orthovanadate takes place.

After this reaction time, the sol obtained is brought back to ambient temperature then it is diluted 20 times.

Then, said diluted sol is left for 30 minutes in an ultrasonic bath in order to assure good dispersion of the particles in aqueous phase.

Then the diluted sol undergoes an operation of dialysis against deionized water in order to remove the salts.

The water is renewed twice a day for three days.

An aqueous sol of nanoparticles of $EuVO_4$ at around pH 6 is finally obtained with a content by weight of inorganic (in other words $EuVO_4$) of around 0.4%, which may optionally be filtered before use.

Example 2

In this example, an aqueous sol of nanoparticles of $Y_{0.5}VO_4Eu_{0.5}$ is prepared in the presence of sodium citrate.

Firstly are prepared aqueous solutions containing the precursors of oxides, namely a solution of europium nitrate, a solution of sodium orthovanadate, and a solution of yttrium nitrate, then these solutions of precursors are mixed with a solution of sodium citrate at 60° C.

The solution of europium nitrate, the concentration of which is 0.1 M, is prepared by dissolution of 0.86 g of $Eu(NO_3)_3$, 5 $H_2O$ in 20 mL of water.

The solution of sodium orthovanadate, the concentration of which is 0.1 M, is prepared from 0.55 g of $Na_3VO_4$ which are poured into 30 mL of water. The pH of the solution of $Na_3VO_4$ is controlled and adjusted if necessary to a value comprised between 12.3 and 12.8 by addition of sodium hydroxide.

The solution of yttrium nitrate, the concentration of which is 0.1 M, is prepared from 0.77 g of $Y(NO_3)_3$, 6 $H_2O$ and 20 mL of water.

The solution of sodium citrate, the concentration of which is 0.1 M, is obtained by dissolution of 0.88 g of $C_6H_5Na_3O_7$, 2 $H_2O$ in 30 mL of water.

The solutions of europium nitrate and yttrium nitrate are mixed and introduced into a round-bottomed two-necked flask surmounted by a condenser and a dropping funnel.

The solution of sodium citrate is placed in this dropping funnel and is then added dropwise to the contents of the round-bottomed two-necked flask, under magnetic stirring.

A white precipitate of lanthanide citrate then forms.

The solution of sodium orthovanadate is placed in the dropping funnel.

The white precipitate of lanthanide citrate is then completely dissolved by addition, dropwise, of the solution of sodium orthovanadate to the contents of the round-bottomed two-necked flask under magnetic stirring.

After the complete addition of the different reagents, the sol is left stirring at 60° C. for 30 minutes during which time the reaction between europium nitrate, sodium orthovanadate and yttrium nitrate takes place.

After this reaction time, the sol obtained is brought back to ambient temperature then it undergoes an operation of dialysis against deionized water for three days, while renewing the water twice a day in order to eliminate the salts and the excess of sodium citrate.

A stable, transparent and colorless aqueous sol of nanoparticles of $Y_{0.5}VO_4{:}Eu_{0.5}$ is then obtained at around pH 7.5 with a content by weight of inorganic $(Y_{0.5}VO_4Eu_{0.5})$ of around 0.5%.

Example 3

In this example, a hydro-organic sol of $Y_{0.5}VO_4Eu_{0.5}$ nanoparticles is prepared.

The aqueous sol of $Y_{0.5}VO_4Eu_{0.5}$ nanoparticles of example 2 is placed in a semi-permeable membrane then it undergoes an operation of dialysis against a solution containing a mixture of water and acetonitrile in equal proportions.

The final sol keeps the stability as well as the fluorescence properties of the aqueous sol but enables the solubilization of organic peroxides such as TATP for example.

Example 4

In this example, a thin film constituted of nanoparticles of $EuVO_4$ is prepared.

In order to form a thin film of $EuVO_4$ from the sol of example 1, it is necessary to perform a transfer of particles in an organic solvent.

The solvent commonly used for the implementation of thin layers is ethanol, or an ethanol-water mixture.

The sol of example 1 thus undergoes an operation of dialysis against a mixture composed of 90% of absolute ethanol and 10% of deionized water for 24 hours, whereby a hydro-alcoholic sol is obtained.

The two faces of a substrate constituted of a glass slide, of microscope slide type, are coated by dip coating of the substrate in the hydro-alcoholic sol obtained above at a rate of 15 cm·min$^{-1}$ or by spin coating at a speed of 800 rpm.

A drying is carried out for 5 minutes in the open air in order to eliminate the solvents from the layer formed.

Example 5

In this example, the effect of solutions of $H_2O_2$ having various concentrations on the emission spectrum of a colloidal solution of $EuVO_4$ is studied.

To observe the effect of a solution of $H_2O_2$ on the emission spectrum of a colloidal solution of $EuVO_4$, quartz vessels containing a constant liquid volume of 2.9 mL are prepared.

They contain 1.5 mL of colloidal solution, a variable quantity of hydrogen peroxide, namely 6, 12, 24, 36, 48, 60, 120, 241, 362, and 1508 ppmv of $H_2O_2$, and are made up with water.

A vessel contains only 1.5 mL of colloidal solution without hydrogen peroxide.

Emission spectra of the solutions: they are acquired by a Horiba Jobin Yvon Fluoromax-P® spectrofluorometer.

The excitation wavelength used is 270 nm. The aperture of the monochromators inlet slots is adjustable (1 to 5 nm). It is chosen as a function of the emission intensity of the solutions in order to obtain a sufficient signal, without saturating the detector. The quartz vessels are positioned in the sample holder of the spectrofluorometer.

Figure 1:
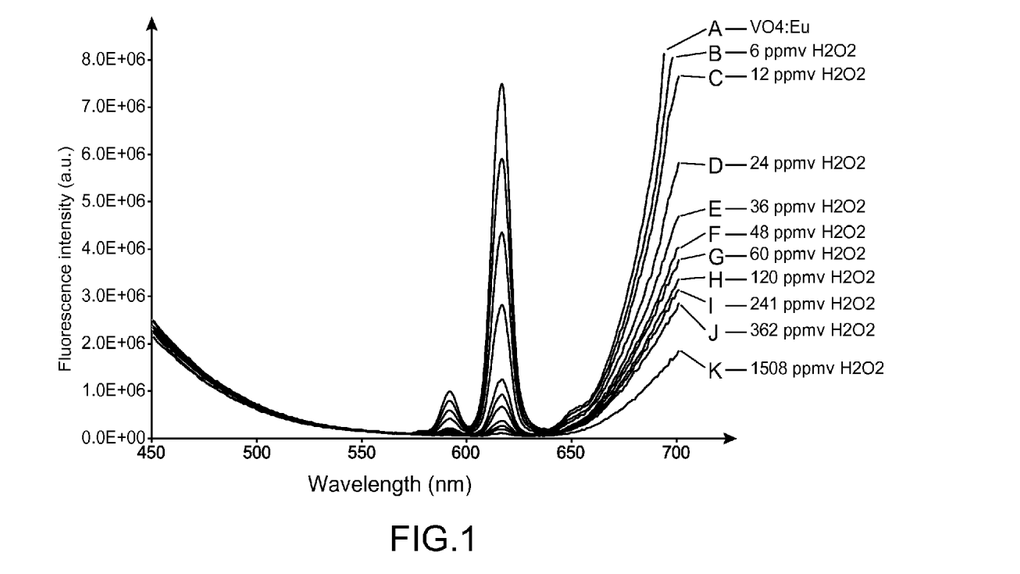
FIG. 1 is a graph that shows fluorescence emission spectra, realized in example 5, representing the evolution of the fluorescence emission as a function of the wavelength as it is observed for colloidal solutions of nanoparticles of $EuVO_4$ not containing hydrogen peroxide (curve A) or variable quantities of $H_2O_2$ of 6, 12, 24, 36, 48, 60, 120, 241, 362, 1508 ppmv (curves B, C, D, E, F, G, H, I, J, K).

The emission spectra obtained are shown in FIG. 1.

FIG. 1 clearly highlights the affinity between the sensitive material and hydrogen peroxide in solution.

Example 6

In this example, the absorption (FIG. 2A) and emission (FIG. 2B) spectra are taken of a solid thin film constituted of nanoparticles of $EuVO_4$ such as that prepared in example 4.

The acquisition protocols of the absorption and emission spectra are presented below.

Absorption spectra of the films: they are acquired by a Perkin Elmer Lambda 900® spectrometer.

A standard scanning is used between 800 and 200 nm in transmission, with an interval between the data of 1 nm. The blank is made with air.

Emission spectra of the films: they are acquired by a Horiba Jobin Yvon Fluoromax-P® spectrofluorometer.

The excitation wavelength used is 270 nm. The aperture of the monochromators inlet slots is adjustable (1 to 5 nm). It is chosen as a function of the emission intensity of the films in order to obtain a sufficient signal, without saturating the detector. The quartz substrate on which is deposited the film is positioned in the measuring chamber with a tilt angle of 45° with respect to the excitation incident beam.

Figure 2A:
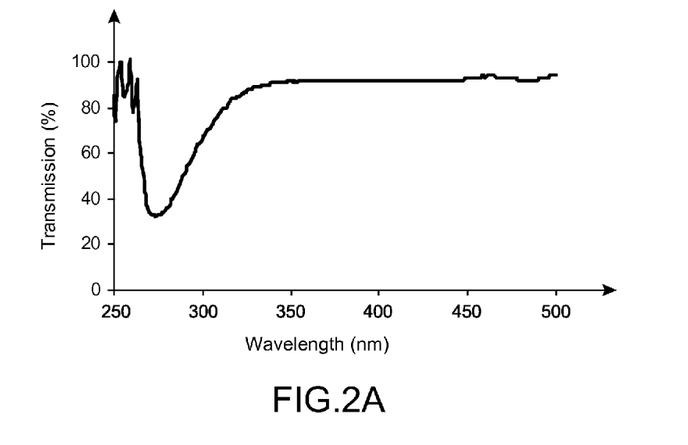
Figure 2B:
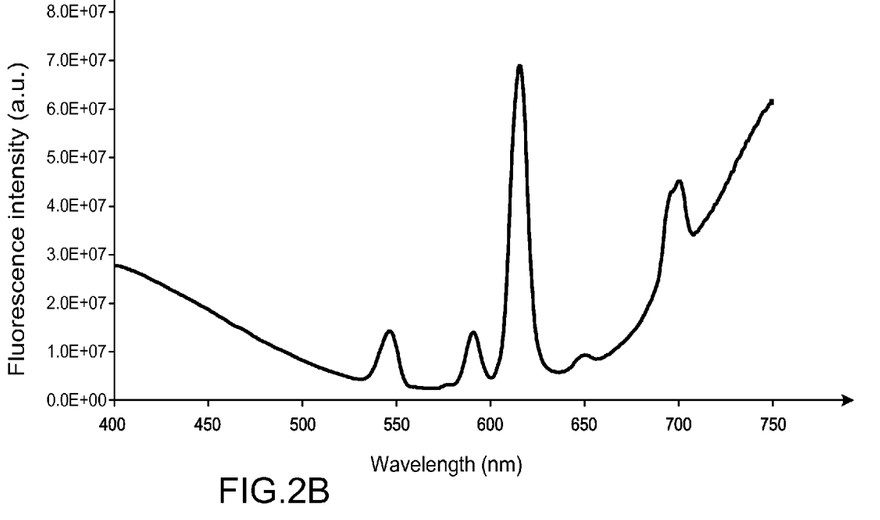

The absorption and emission spectra are shown respectively in FIGS. 2A and 2B.

It should be noted that these spectra relate to $EuVO_4$ but that the spectra are similar whatever the Eu content.

Example 7

In this example, the detection of vapors of hydrogen peroxide is carried out using an optical sensor comprising a thin film constituted of nanoparticles of $EuVO_4$.

A spectrofluorometer is used in "kinetic" mode, which makes it possible to measure the fluorescence intensity at a given wavelength, referred to as measurement wavelength, under a given excitation wavelength, as a function of time.

The excitation wavelength used is 270 nm whereas the measurement wavelength is 617 nm.

Figures 3, 4:
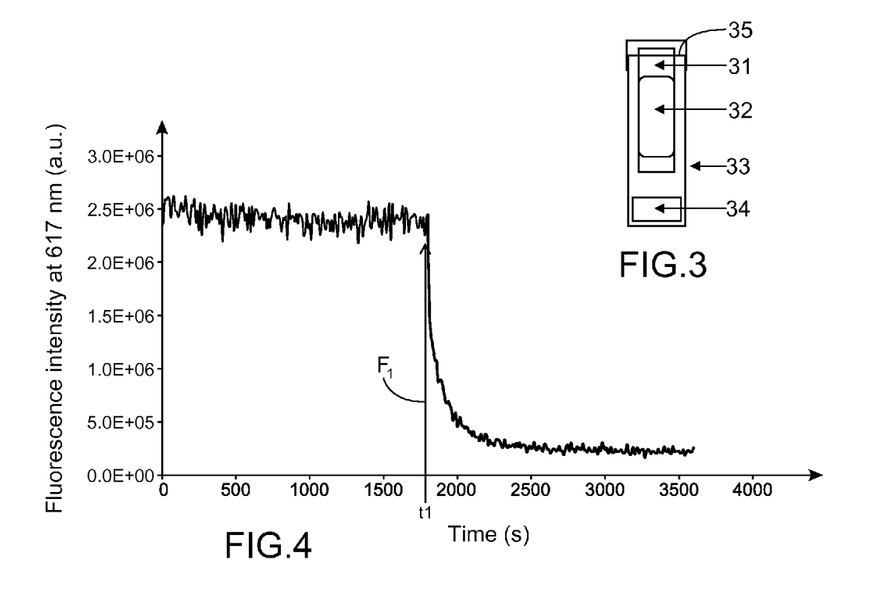
FIG. 3 represents a schematic vertical sectional view of the device used for the tests for detecting vapors of $H_2O_2$. This assembly makes it possible to subject the optical sensor to an atmosphere saturated with peroxide.
FIG. 4 represents the evolution of the fluorescence intensity at 617 nm, after excitation at 270 nm, as observed for an optical sensor comprising a solid thin film constituted of nanoparticles of $EuVO_4$, when said sensor is successively exposed to ambient air then to vapors of hydrogen peroxide.

As is represented in FIG. 3, a glass substrate (31), on which a film of $EuVO_4$ (32) has been deposited beforehand as has been described in example 4, is introduced into a quartz vessel (33), which is itself positioned in the sample holder of the spectrofluorometer (Horiba Jobin Yvon FluoroMax®)

All of the measurements are carried out at ambient temperature and according to the protocol described previously.

The kinetic measurement is started in order to check the stability of the fluorescence intensity of the film in the absence of vapors of hydrogen peroxide.

After 30 minutes of exposure to UV, the quartz vessel is saturated with vapors of $H_2O_2$ by pouring 0.5 mL of a 17.5% by volume aqueous solution of $H_2O_2$ into the bottom thereof, without the solution of $H_2O_2$ (34) entering into contact with the film as is illustrated in FIG. 3.

The vessel is then rapidly closed using Parafilm® (35) in order to continue the kinetic measurement.

The reduction in fluorescence at 617 nm due to the interaction between the film of $EuVO_4$ and the vapors of $H_2O_2$ is then measured.

FIG. 4 represents the fluorescence intensity in the absence, then in the presence, of hydrogen peroxide vapors. For the first 1800 seconds, the film of $EuVO_4$ is not exposed to $H_2O_2$ in order to check the stability of the fluorescence intensity of the film.

After 1800 seconds (time t1 in FIG. 4), the hydrogen peroxide solution is introduced into the vessel (arrow F1 on FIG. 4), which is immediately closed. The fluorescence intensity then drops considerably.

Example 8

In this example, the selectivity of an optical sensor comprising a thin film constituted of nanoparticles of $EuVO_4$ vis-à-vis peroxides is highlighted.

A spectrofluorimeter is used in "kinetic" mode, which makes it possible to measure the fluorescence intensity at a given wavelength, referred to as measurement wavelength, under a given excitation wavelength, as a function of time.

The excitation wavelength used is 270 nm, whereas the measurement wavelength is 617 nm.

A glass substrate, on which a film of $EuVO_4$ has been deposited previously as has been described in example 4, is introduced into a quartz vessel, which is itself positioned in the sample holder of the spectrofluorometer (Horiba Jobin Yvon FluoroMax®)

All of the measurements are carried out at ambient temperature and according to the protocol described previously.

The kinetic measurement is started in order to check the stability of the fluorescence intensity of the film.

After 10 minutes, the quartz vessel is saturated with vapors of an organic solvent by pouring 0.5 mL of the solvent into the bottom of the quartz vessel without the solvent entering into contact with the film as in example 7.

The vessel is then rapidly closed using Parafilm® and the kinetic measurement is continued. The evolution of the fluorescence at 617 nm of the film of $EuVO_4$ is thus measured in the presence of an atmosphere saturated with the vapors of the solvent.

Three tests are carried out each time with a different solvent, namely ethanol, acetone, then toluene.

Let $I_0$ be the fluorescence intensity at 617 nm of the film of $EuVO_4$ at time $t_0$, and I the fluorescence intensity of the same film at 617 nm at time t.

Figure 5:
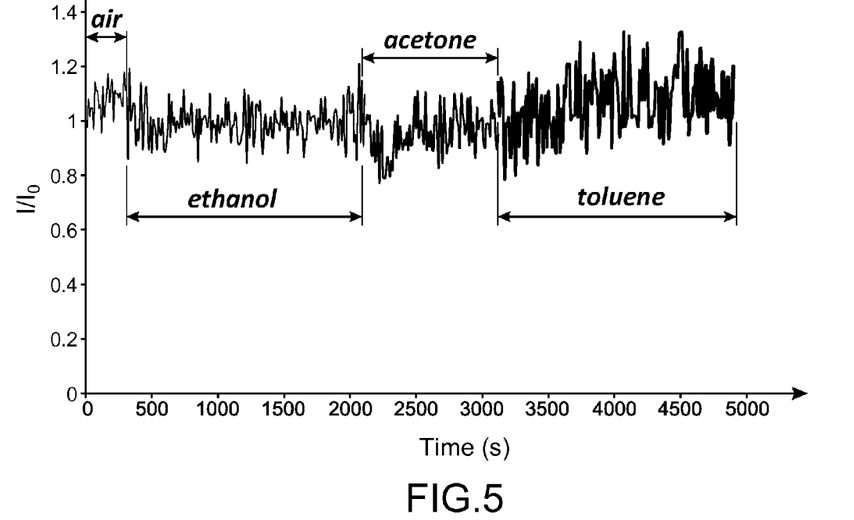
FIG. 5 represents the evolution of the fluorescence intensity at 617 nm, after excitation at 270 nm, as observed for an optical sensor comprising a solid thin film constituted of nanoparticles of $EuVO_4$ when said sensor is exposed to ambient air or to vapors of volatile organic compounds, namely ethanol, acetone, and toluene vapors.

FIG. 5 represents the evolution of $I/I_0$ as a function of time in seconds, in the presence of a solvent (ethanol, acetone or toluene) in the bottom of the vessel or when the sensor is simply exposed to ambient air before addition of any interferent (interfering compound).

The measurements in the presence of the different solvents and in ambient air were carried out separately but are reported on the same graph in order to facilitate comparison.

The $I/I_0$ ratio remains globally constant. The sensor is thus selective vis-à-vis peroxides and the solvents do not create any interference.

Example 9

In this example, a glass substrate, on which a film of $EuVO_4$ has been deposited beforehand as has been described in example 4, is introduced into a quartz vessel, which is itself positioned in the sample holder of the spectrofluorometer (Horiba Jobin Yvon FluoroMax®).

All of the measurements are carried out at ambient temperature and according to the previously described protocol.

Figure 6:
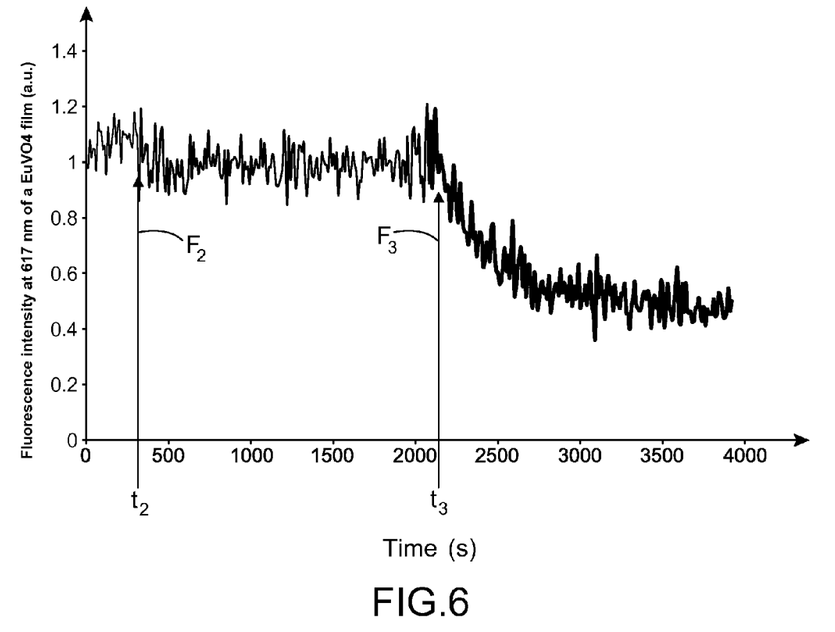
FIG. 6 represents the evolution of the fluorescence intensity at 617 nm, after excitation at 270 nm, as observed for an optical sensor comprising a thin film constituted of nanoparticles of $EuVO_4$ when said sensor is successively exposed to ambient air, to vapors of ethanol then to vapors of hydrogen peroxide.

The film is firstly exposed to ambient air, up to a time t2 (300 s), at which ethanol is introduced into the vessel (arrow F2 of FIG. 6).

After the exposure of the sensor to vapors of ethanol for 1800 seconds, several drops of hydrogen peroxide are introduced (arrow F3 of FIG. 6) into the vessel at time t3 (2100 s), still without the film entering into contact with the liquid.

The measurement of the fluorescence intensity of the film of $EuVO_4$ is continued and its variations are reported on FIG. 6.

This figure thus represents the evolution of the $I/I_0$ ratio as a function of time when the film is placed in the empty vessel for 300 seconds, in the presence of ethanol for 1800 seconds, then in the presence of hydrogen peroxide for 2100 seconds.

FIG. 6 shows that the fluorescence intensity drops after exposure to hydrogen peroxide. This indicates that the sensor offers good sensitivity and very high specificity with regard to peroxides despite the presence of organic solvents.

Example 10

In this example, the performance stability over time of an optical sensor comprising a thin film constituted of nanoparticles of $EuVO_4$ is highlighted.

In this example, a sensor identical to that of examples 4 and 7 to 9 is used.

The day it is made, the sensor is exposed to vapors of hydrogen peroxide, in saturated atmosphere in the measurement vessel, for 10 minutes.

The value of the fluorescence intensity is then noted $I_0$. Said sensor is then stored for 100 days in ambient air and in daylight. A new measurement is then carried out under exposure of vapors saturated with hydrogen peroxide for 5 minutes. The fluorescence intensity is then measured.

Since the values $I_0$ and $I_{100}$ are identical, of the order of $(1.3\pm0.1)\cdot10^7$, it may be concluded that the fluorescence performances of the sensor are stable over long time periods, greater than 3 months here, and without taking particular precautions with regard to the conservation conditions of said sensor unlike the usual organic materials. The fluorescence intensity at 617 nm of a film of $EuVO_4$ excited at 270 nm is thus conserved despite storage in air and in daylight. The material thus has a lifetime greater than three months under exposure to daylight.

REFERENCES

[1] S. Yao, S. Yuang, J, Xu, Y. Wang, J. Luo, S. Hu, *Applied Clay Science*, 33, 35, 2006
[2] (a) J. G. Hong, J. Maguhn, D. Freitag, A. Kettrup, Fresenius *J. Anal. Chem.*, 361, 124, 1998 (b) R. Schulte-Ladbeck, P. Kolla, U. Karst, *Analyst*, 127, 1352, 2002
[3] D. Lu, A. Cagan, R Minoz, T. Tangkuaram, J. Wang, *Analyst*, 131, 1279, 2006
[4] F. Bohrer, C. Colesniuc, J. Park, I. Schuller, A. Kummel, W. Trogler, *Journal of American Chemical Society*, 130, 3712, 2008
[5] C. Guzman, G. Orozco, Y. Verde, S. Jimenez, L. A. Godinez, E. Juaristi, E. Bustos, *Electrochimica Acta*, 54, 1728, 2009
[6] D. Laine, C. Roske, F. Cheng, *Anal. Chim. Acta*, 608, 56, 2008
[7] R. Munoz, D. Lu, A. Cagan, J. Wang, *Analyst*, 132, 560, 2007
[8] A. Mills, P. Grosshans, E. Snadden, *Sensors and Actuators B*, 136, 458, 2009
[9] A. Apblett, B. Kiran., S. Malka, N. Materer, A. Piquette, *Ceram Trans*, 172, 29, 2005
[10] J. Sanchez, W. Trogler, *Journal of Material Chemistry*, 18, 5134, 2008
[11] M. Germain, M. Knapp, *Inorganic Chemistry*, 47, 9748, 2008
[12] S. Malashikhin, N. Finney, *Journal of the American Society*, 130, 12846, 2008
[13] X. Shu, Y. Chen, H. Yuang, S. Gao, D. Xiao, *Anal. Chem.*, 79(10), 3695, 2007
[14] D. Casanova, C. Bouzigues, T. L. Nguyen, R. O. Ramodiharilafy, L. Bouzhir-Sima, T. Gacoin., J. P. Boilot, P. L. Tharaux, A. Alexandrou, *Nature Nanotechnology*, 4, 581, 2009
[15] P. Belleville, C R. *Chimie*, 13, 97, 2010
[16] H. Althues, P. Simon, S. Kaskel, *Journal of Material Chemistry*, 17, 758, 2007
[17] M. Yu, J. Lin, F. Fang, *Chemistry of Materials*, 17, 1783, 2005
[18] Q. Zhou, L. Zhang, H. Fan, L. Wu, Y. Lv, *Sensors and Actuators B*, 144, 192, 2010
[19] FR-A-2 703 791
[20] Rouquérol et al., *Pure & Applied Chemistry*, 66(8), 1994, pages 1739-1758
[21] Sanchez-Pedrono, *Anal. Chem. Acta*, 182, 285, 1986
[22] B. Valeur, *Molecular Fluorescence: Principles and Applications*, Ed. WILEY VCH, New York, 2002.

The invention claimed is:

1. A method for detecting or assaying vapors of one or more target compound(s) or molecule(s) comprising utilizing nanoparticles of at least one oxide of at least one transition metal doped with a rare earth element, obtained through a sol-gel process, as a sensitive material in a chemical sensor; wherein the nanoparticles are present in the chemical sensor in the form of a solid thin film of nanoparticles of a thickness of 2 nanometers to one micrometer, and wherein said one or more target compound(s) or molecule(s) is (are) detected or assayed by measuring variations of physical property(ies) of the solid thin film of nanoparticles induced by the presence of said one or more target compound(s) or molecule(s).

2. The method of claim 1, wherein the thin film is prepared directly by wet process by deposition of an aqueous sol which is the sol from which the nanoparticles have been obtained.

3. The method of claim 1, wherein the solid thin film of nanoparticles covers at least in part one or both faces of a flat substrate.

4. The method of claim 1, wherein the solid thin film of nanoparticles has a thickness of 100 nm to 300 nm.

5. The method of claim 1, wherein the solid thin film of nanoparticles is a mesoporous film.

6. The method of claim 1, wherein the solid thin film of nanoparticles has a specific surface area of 100 $m^2/g$ to 200 $m^2/g$, measured by BET.

7. A method for detecting or assaying vapors of one or more target compound(s) or molecule(s) comprising utilizing nanoparticles of at least one oxide of at least one transition metal doped with a rare earth element, obtained through a sol-gel process, as a sensitive material in a chemical sensor; wherein the nanoparticles are present in the chemical sensor in the form of a sol of nanoparticles in a solvent, and wherein said one or more target compound(s) or molecule(s) is (are) detected or assayed by measuring variations of physical property(ies) of the sol of nanoparticles in a solvent induced by the presence of said one or more target compound(s) or molecule(s).

8. The method of claim 7, wherein the sol of nanoparticles has a concentration of nanoparticles of 0.01% to 4% by weight.

9. The method of claim 7, wherein the solvent is selected from the group consisting of water, organic solvents; and mixtures thereof.

10. The method of claim 7, wherein the sol of nanoparticles is sprayed in the form of a jet, nebulisate or spray.

11. The method of claim 7, wherein the sol of nanoparticles is in the form of a thin film.

12. The method of claim 11, wherein the thin film of the sol of nanoparticles has a thickness of 2 nanometers to one micrometer.

13. The method of claim 1, wherein the nanoparticles are nanoparticles of $Y_xVO_4Eu_{1-x}$, where x has a value of 0 to 0.995.

14. The method of claim 1, wherein the nanoparticles are selected from the group consisting of nanoparticles of $EuVO_4$, and nanoparticles of $Y_{0.5}VO_4Eu_{0.5}$.

15. The method of claim 1, wherein the nanoparticles have a diameter of 2 to 100 nm.

16. The method of claim 1, wherein the nanoparticles of at least one oxide of at least one transition metal doped with a rare earth element are each covered with a thin layer of silica obtained through a sol-gel process.

17. The method of claim 16, wherein the thin layer of silica has a thickness of 1 to 10 nanometers.

18. The method of claim 16, wherein the silica is functionalized by chemical groups.

19. The method of claim 1, wherein the chemical sensor is a gravimetric sensor.

20. The method of claim 1, wherein the chemical sensor is a fluorescence optical sensor.

21. The method of claim 1, wherein the sensor is a multisensor comprising several elementary sensors selected from fluorescence optical sensors and gravimetric sensors, at least one among said elementary sensors being a sensor that comprises nanoparticles of at least one oxide of at least one transition metal doped with a rare earth element, obtained through a sol-gel process, as a sensitive material.

22. The method of claim 1, wherein the target compound(s) or molecules(s) are selected from the group consisting of atmospheric pollutants, explosives and precursors of explosives.

23. The method of claim 1, wherein the target compound(s) or molecules(s) are selected from peroxides.

24. The method of claim 23, comprising detecting or assaying peroxides vis-à-vis volatile organic compounds.

25. The method of claim 23, wherein the target compound(s) or molecules(s) are selected from the group consisting of hydrogen peroxide, hydroperoxides, and peroxides of ketones.

26. A chemical sensor comprising nanoparticles of at least one oxide of at least one transition metal doped with a rare earth element, obtained through a sol-gel process, as a sensitive material; in which the nanoparticles are present in the chemical sensor in the form of a solid thin film of nanoparticles of a thickness of 2 nanometers to one micrometer.

27. A chemical sensor comprising nanoparticles of at least one oxide of at least one transition metal doped with a rare earth element, obtained through a sol-gel process, as a sensitive material; in which the nanoparticles are present in the chemical sensor in the form of a sol of nanoparticles in a solvent.

28. The chemical sensor according to claim 26, wherein the chemical sensor is a gravimetric sensor.

29. The chemical sensor according to claim 27, wherein the chemical sensor is a gravimetric sensor.

30. The chemical sensor according to claim 26, wherein the chemical sensor is a fluorescence sensor.

31. The chemical sensor according to claim 27, wherein the chemical sensor is a fluorescence sensor.

32. The chemical sensor according to claim 26, wherein the chemical sensor detects hydrogen peroxide.

33. The chemical sensor according to claim 27, wherein the chemical sensor detects hydrogen peroxide.

34. The method of claim 7, wherein the nanoparticles are nanoparticles of $Y_xVO_4Eu_{1-x}$, where x has a value of 0 to 0.995.

35. The method of claim 7, wherein the nanoparticles are selected from the group consisting of nanoparticles of $EuVO_4$, and nanoparticles of $Y_{0.5}VO_4Eu_{0.5}$.

36. The method of claim 7, wherein the nanoparticles have a diameter of 2 to 100 nm.

37. The method of claim 7, wherein the nanoparticles of at least one oxide of at least one transition metal doped with a rare earth element are each covered with a thin layer of silica obtained through a sol-gel process.

38. The method of claim 37, wherein the thin layer of silica has a thickness of 1 to 10 nanometers.

39. The method of claim 37, wherein the silica is functionalized by chemical groups.

40. The method of claim 7, wherein the chemical sensor is a gravimetric sensor.

41. The method of claim 7, wherein the chemical sensor is a fluorescence optical sensor.

42. The method of claim 7, wherein the sensor is a multisensor comprising several elementary sensors selected from fluorescence optical sensors and gravimetric sensors, at least one among said elementary sensors being a sensor that comprises nanoparticles of at least one oxide of at least one transition metal doped with a rare earth element, obtained through a sol-gel process, as a sensitive material.

43. The method of claim 7, wherein the target compound(s) or molecules(s) are selected from the group consisting of atmospheric pollutants, explosives and precursors of explosives.

44. The method of claim 7, wherein the target compound(s) or molecules(s) are selected from peroxides.

45. The method of claim 44, comprising detecting or assaying peroxides vis-à-vis volatile organic compounds.

46. The method of claim 44, wherein the target compound(s) or molecules(s) are selected from the group consisting of hydrogen peroxide, hydroperoxides, and peroxides of ketones.

47. The method of claim 9, wherein the organic solvent is selected from the group consisting of C1 to C6 aliphatic alcohols, acetonitrile, tetrahydrofuran, toluene; and mixtures thereof.

48. The method of claim 11, wherein the thin film is covering at least in part one or both faces of a flat substrate.

* * * * *

UNITED STATES PATENT AND TRADEMARK OFFICE
CERTIFICATE OF CORRECTION

PATENT NO. : 9,964,528 B2
APPLICATION NO. : 14/347918
DATED : May 8, 2018
INVENTOR(S) : Franck Pereira et al.

It is certified that error appears in the above-identified patent and that said Letters Patent is hereby corrected as shown below:

On the Title Page

Item (*) Notice: "Subject to any disclaimer, the term of this patent is extended or adjusted under 35 U.S.C. 154 (b) by 0 days. days." should be -- Subject to any disclaimer, the term of this patent is extended or adjusted under 35 U.S.C. 154(b) by 0 days. --.

In the Specification

Column 15, Line 13, "$Y_xO_4$" should be -- $Y_xVO_4$ --.

Column 15, Line 14, "$Y_xO_4$" should be -- $Y_xVO_4$ --.

Column 15, Line 42, "$Y_xO_4$" should be -- $Y_xVO_4$ --.

Signed and Sealed this
Thirty-first Day of July, 2018

Andrei Iancu
*Director of the United States Patent and Trademark Office*